United States Patent
Wall et al.

(10) Patent No.: US 12,268,789 B2
(45) Date of Patent: Apr. 8, 2025

(54) WORK SPACE DISINFECTION APPARATUS AND METHOD

(71) Applicant: Knoll, Inc., East Greenville, PA (US)

(72) Inventors: Roger Wall, Getzville, NY (US); Joe Carere, Getzville, NY (US); Carl Magnusson, New York, NY (US)

(73) Assignee: Knoll, Inc., East Greenville, PA (US)

( * ) Notice: Subject to any disclaimer, the term of this patent is extended or adjusted under 35 U.S.C. 154(b) by 427 days.

(21) Appl. No.: 17/687,034

(22) Filed: Mar. 4, 2022

(65) Prior Publication Data

US 2022/0288252 A1  Sep. 15, 2022

Related U.S. Application Data

(60) Provisional application No. 63/159,038, filed on Mar. 10, 2021.

(51) Int. Cl.
*A61L 2/10* (2006.01)
*A61L 2/24* (2006.01)

(52) U.S. Cl.
CPC ........ *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC .......... A61L 2/10; A61L 2/24; A61L 2202/11; A61L 2202/14; A61L 2202/25
See application file for complete search history.

(56) References Cited

U.S. PATENT DOCUMENTS

| | | |
|---|---|---|
| 2,287,079 A | 6/1942 | Anderson |
| D164,734 S | 10/1951 | Quinn |
| 2,821,450 A | 1/1958 | Knoll |
| 3,777,437 A | 12/1973 | Christen |
| 5,094,174 A | 3/1992 | Grund et al. |
| 5,111,770 A | 5/1992 | Weelink |
| 5,155,955 A | 10/1992 | Ball et al. |
| 5,287,909 A | 2/1994 | King et al. |
| 5,921,040 A | 7/1999 | Glashouwer et al. |

(Continued)

OTHER PUBLICATIONS

International Search Report for PCT/US2022/019102 dated Jun. 23, 2022.

(Continued)

*Primary Examiner* — David A Vanore

(74) *Attorney, Agent, or Firm* — Buchanan Ingersoll & Rooney PC

(57) ABSTRACT

Disinfection devices positionable to disinfect work spaces within an office of an office building or other work area can be configured or incorporated into a lighting device, ceiling mounted device, baffle, furniture, or other type of disinfection device. Embodiments can be configured to utilize UVC-222 light or other UVC light to disinfect the work area. In some embodiments, the disinfecting light can be applied at a pre-selected time of night when the work area is expected to have no staff or limited numbers of staff therein. The distribution of the disinfection light can be configured to help ensure application of the light for a pre-selected time period applies at least a pre-selected dose of the light to the work area for sufficient, if not complete, disinfection of objects within the work area that include papers, furniture, and other items.

17 Claims, 10 Drawing Sheets

(56) References Cited

U.S. PATENT DOCUMENTS

| | | | |
|---|---|---|---|
| 6,000,180 | A | 12/1999 | Goodman et al. |
| 6,021,613 | A | 2/2000 | Reuter et al. |
| 6,073,399 | A | 6/2000 | Shipman et al. |
| 6,625,935 | B1 | 9/2003 | King et al. |
| 8,365,798 | B2 | 2/2013 | Feldpausch et al. |
| 10,894,104 | B1 | 1/2021 | Kim et al. |
| 10,987,440 | B1 | 4/2021 | Sood et al. |
| 2002/0189180 | A1 | 12/2002 | King et al. |
| 2009/0004046 | A1* | 1/2009 | McEllen ................ H05B 41/39 422/2 |
| 2009/0129974 | A1* | 5/2009 | McEllen ................ A61L 9/205 422/108 |
| 2015/0062893 | A1 | 3/2015 | Lynn et al. |
| 2017/0296686 | A1 | 10/2017 | Cole |
| 2020/0147249 | A1* | 5/2020 | Hussein ................... A61L 2/16 |
| 2020/0188542 | A1 | 6/2020 | Lei et al. |
| 2020/0215215 | A1 | 7/2020 | Randers-Pehrson et al. |
| 2020/0282086 | A1* | 9/2020 | Silverman ............... A61L 9/015 |
| 2020/0282089 | A1 | 9/2020 | Lei et al. |
| 2021/0364178 | A1* | 11/2021 | Kiviat ..................... F24F 3/163 |
| 2021/0403294 | A1* | 12/2021 | Szczepkowski ...... B66C 13/085 |
| 2022/0152237 | A1* | 5/2022 | Barrios Sierra .......... A61L 2/10 |
| 2022/0305159 | A1* | 9/2022 | Collet ...................... A61L 9/20 |
| 2023/0053659 | A1* | 2/2023 | Hood ....................... A61L 2/10 |
| 2023/0056649 | A1* | 2/2023 | Hood ..................... H05B 47/11 |

OTHER PUBLICATIONS

Written Opinion of the International Searching Authority for PCT/US2022/019102 dated Jun. 23, 2022.

\* cited by examiner

WORK SPACE DISINFECTION APPARATUS AND METHOD

CROSS-REFERENCE TO RELATED APPLICATIONS

This application claims priority to U.S. Provisional Patent Application No. 63/159,038, filed on Mar. 10, 2021.

FIELD

Embodiments of the present invention relate to furniture systems, ceiling mounted devices, baffles, furniture, lighting, disinfection devices positionable to disinfect work spaces within an office of an office building or other work area. Embodiments of the present invention also relate to methods of making and using such apparatuses.

BACKGROUND

Furniture systems can be utilized in a number of different settings. In office settings, cubicle systems are often used to partition a work space into a number of different work areas. For example, cubicle partitions and privacy screens may be utilized to help define different work areas within a floor of an office building. Examples of such cubicle partitions and privacy screens can be appreciated from U.S. Pat. Nos. 2,287,079, 2,821,450, 3,777,437, 5,094,174, 5,111,770, 5,155,955, 5,287,909, 5,921,040, 6,000,180, 6,021,613, 6,073,399, 6,625,935, 8,365,798, and D164,734, and U.S. Patent Application Publication Nos. 2002/0189180 and 2009/029339.

Work spaces can be designed to be relatively open. Such arrangements can have significant cleaning requirements to keep work spaces relatively safe for use. Often, a cleaning service or a staff of cleaning personnel (e.g. janitors, etc.) are utilized to help keep such places clean for use. This personnel may need to use cleaning devices as well as sprays or other cleaning agents that can include chemical agents. Some personnel may be allergic to such cleaning agents or have other sensitivity to such agents that can pose a health risk or at least an inconvenience to them.

SUMMARY

Furniture systems, furniture, lighting, ceiling mounted devices, baffles, disinfection devices positionable to disinfect work spaces within an office of an office building or other work area and methods of making and using the same can provide an improvement in the efficiency and reliability of cleaning operations for disinfecting a particular work area. Such embodiments can be designed and employed to reduce staffing requirements or external costs associated with cleaning or disinfecting of the work space while also providing improvement in the quality of disinfection of the work area and an improvement in the extent to which the work area is disinfected. The disinfection can also be performed without requiring the use of chemical agents or sprays, which can provide additional health benefits to the users of the work space or work area.

A disinfection device positionable within a work area is provided. Some embodiments of the device can be utilized in ceiling tiles, baffles, or other fixtures that can be connected to or mounted to a ceiling of an office or room of an office or other type of work area within an office building on a floor of the office building. Embodiments of the disinfection device can include a housing, a controller positioned in the housing, and a lamp having an ultraviolet (UV) light emission device connected to the housing. The controller can be connected to the lamp to control an output of UV light from the UV light emission device to a work space within the work area. The output of the UV light emittable from the UV light emission device can have a light distribution area within the work space or work area.

The UV light can be a non-visible light within the UV emission range. For instance, the UV light can have a wavelength between 100 nanometers (nm) and 400 nm. In some preferred embodiments, the UV light has a wavelength that is between 200 nm and 225 nm or is 222 nm.

Embodiments of the disinfection device can also include a plurality of light emitting diodes (LEDs) connectable to the housing. The LEDs can include a first LED that is illuminable in a first color, a second LED illuminable in a second color, and a third LED illuminable in a third color. The first, second, and third colors can all be different colors (e.g. the first color can be red, the second color can be green, and the third color can be blue or purple). For instance, this first color can differ from the second color and can also differ from the third color. The second color can also differ from the third color.

Embodiments of the disinfection device can include other elements. For example, the device can also include at least one sensor connected to the housing to detect motion within the work area. The motion that can be detected can include motion of an object within the distribution of light area for a UV light emitting device of the disinfection device and/or motion of an object near the distribution of light area. The controller can be configured so that, in response to detecting a lack of motion for a pre-selected vacancy period of time within the work space (e.g. a pre-selected vacancy time period), the controller can activate the lamp so that the UV light emission device is activated to provide the UV light to the distribution of light area within the work space for a pre-selected disinfection time period.

The controller can also be configured so that, in response to the sensor detecting occupant motion while the UV light emission device is actively emitting UV light, the controller deactivates the UV light emission device to stop output of the UV light and interrupt disinfection occurring within the pre-selected disinfection time period. The controller can also be configured so that, after the disinfection occurring within the pre-selected disinfection time period is interrupted, disinfection via emission of the UV light by the UV light emission device resumes where it left off in response to no motion within the work space being detected for the pre-selected vacancy time that occurs after interruption of the disinfection. This type of configuration can result in the UV light being emitted for a cumulative time period of the pre-selected disinfection time period in spite of the output of UV light being interrupted due to detected motion one or more times. The controller can also, or alternatively, be configured so that, after the disinfection occurring within the pre-selected disinfection time period is interrupted, the controller activates the UV light emission device to apply the UV light continuously for an entirety of the pre-selected disinfection time period in response to no occupant motion being detected for the pre-selected vacancy time after the disinfection was interrupted. This type of configuration can result in the UV light being emitted continuously for the entirety of the pre-selected disinfection time period in spite of the output of UV light being interrupted due to detected motion one or more times (e.g. the overall output of the UV light may be over the disinfection time period due to the stoppages that may occur as a result of detected motion).

The UV light emission device can be considered a first light emission device and the lamp of the disinfection device can also have a second light emission device. The second light emission device can be configured to output visible light to illuminate the work space. It should be appreciated that the light configured to output visible light to illuminate the work space can alternatively be considered a first light emission device and the UV light emission device can alternatively be considered a second light emission device.

In some embodiments, the disinfection device can also include a second light emission device connected to the housing that is configured to output visible light to illuminate the work space. Such a light emission device may not be part of the lamp having the UV light emission device, for example.

The housing of the disinfection device can have a number of different shapes and sizes. For instance, the housing can be rectangular in shape, polygonal in shape, or circular in shape and can be configured to be mounted to a ceiling of a room of an office building.

It should be appreciated that visible light that can be output from a light emission device can be light that is visible to human eyes and can illuminate a dark space (e.g. a dark room at night). The output of visible light can include visible light within the visible light spectrum, for example (e.g. light having a wavelength of between 400 nanometers (nm) and 700 nm or between 400 nm and 780 nm or between 380 nm and 770 nm). The emission of UV light that can be output from a UV light emission device is not visible to the human eye and would not provide such illumination to a darkened space or area.

A method of disinfecting a work area is also provided. Embodiments of the method can include positioning at least one disinfection device adjacent a ceiling of the work area. Each disinfection device can include a housing, a controller positioned in the housing, and a lamp having an ultraviolet (UV) light emission device connected to the housing. The controller can be connected to the lamp to control an output of UV light from the UV light emission device to the work area. The output of UV light emittable from the UV light emission device can have a light distribution area within the work area or a work space of the work area. In response to detecting a lack of motion for a pre-selected vacancy period of time within the area, the lamp of the at least one disinfection device can be activated so that the UV light emission device provides the UV light to the distribution of light area within the work space for a pre-selected disinfection time period.

In some embodiments, the and also determining the current time is within a pre-selected disinfection cycle time period, the lamp of the at least one disinfection device can be activated so that the UV light emission device provides the UV light to the distribution of light area within the work space for a pre-selected disinfection time period in response to multiple different requirements being met. For instance, the actuation of the disinfection device(s) for UV light emission for the pre-selected disinfection time period can occur in response to detecting a lack of motion for a pre-selected vacancy period of time within the area that occurs when the current time is within a pre-selected disinfection cycle time period. This time period can be set for a time range in which the work area is not typically utilized or has low occupancy. For instance, the pre-selected disinfection cycle time period can be between 10 PM and 4 AM, between 9 AM and 5 AM, between 11 PM and 3 AM, or some other suitable daily time range. The method can be performed so that the disinfection cycle that is performable via the one or more disinfection devices can be run each day in this pre-selected time range.

Embodiments of the method can include other steps or elements. For instance, in response to detecting occupant motion while the UV light emission device is actively emitting UV light, the UV light emission device can be deactivated to stop output of the UV light and interrupt disinfection occurring within the pre-selected disinfection time period. After the disinfection occurring within the pre-selected disinfection time period is interrupted, disinfection via emission of the UV light can be resumed where it left off in response to no motion within the work space being detected for the pre-selected vacancy time period that occurs after interruption of the disinfection so the UV light is emitted to the work space for the pre-selected disinfection time period. The running time for UV light emission or disinfection can be tracked so that multiple stoppages due to detected motion are accounted for and the resumption of UV light emissions occurs so that the UV light is emitted for an entirety of the pre-selected disinfection timer period in spite of being stopped due to detection motion one or more times during the cleaning cycle. A controller of the disinfection device can track the UV light emission time period for addressing such a discrete output of the UV light that may occur due to one or more delays that can occur as a result of detected motion. In other situations, after the disinfection occurring within the pre-selected disinfection time period is interrupted, the UV light emission device can be activated to apply the UV light continuously for an entirety of the pre-selected disinfection time period in response to no occupant motion being detected for the pre-selected vacancy time after the disinfection was interrupted.

The method can utilize at least one embodiment of the disinfection device. Some aspects can include use of a sensor to detect occupant motion. In response to detecting the lack of motion for the pre-selected vacancy period of time within the area, the output of visible light in the work space can also be turned off as part of the method. In some embodiments, the visible light that is turned off is a light emitted by another light emitting device of the disinfection device. In other embodiments, the visible light that is turned off can be light that is output from another device. The controller for the disinfection device can be communicatively connected to a switch or other control element for actuating the turning off of such lights in some embodiments.

Embodiments of the method can also include emitting visible light via the lamp of each of the at least one disinfection device to illuminate the work space of the work area. The visible light can be emitted prior to disinfection occurring or after disinfection occurring, for example.

Embodiments of the method can utilize a particular type of UV light. For instance, UVC light that has a wavelength of between 200 nm and 225 nm or has a wavelength of 222 nm can be utilized in some embodiments. Other embodiments may utilize another type of UV light. The UV light that is emitted is usually not be visible to human eyesight.

The method can be utilized in different work area settings. In some embodiments, the work area can be an office in an office building and there can be at least one table positioned in the work space. In other embodiments, the work area can be a floor in an office building and different work spaces can be different rooms or regions within the floor of the office building.

The pre-selected disinfection time period can be defined so this time period is greater than 60 minutes and less than 240 minutes in some embodiments. The UV light emission device can be configured to provide the UV light to the distribution of light area within the work space to provide a dose of at least 6 milliJoules per square centimeter (mJ/cm$^2$) to an entirety of the light distribution area within the pre-selected disinfection time period in some embodiments. This dosing can be configured so that the portions of the distribution of light area farthest from the UV light emission device can receive at least this dose of the UV light.

Other details, objects, and advantages of the furniture, lighting, ceiling mounted devices, baffles, disinfection devices and disinfection processes will become apparent as the following description of certain exemplary embodiments thereof proceeds.

BRIEF DESCRIPTION OF THE DRAWINGS

Exemplary embodiments of furniture, lighting, ceiling mounted devices, baffles, disinfection devices positionable to disinfect work spaces within an office of an office building or other work area and methods of making and using the same are shown in the accompanying drawings. It should be understood that like reference numbers used in the drawings may identify like components.

DETAILED DESCRIPTION OF EXEMPLARY EMBODIMENTS

Figure 1:
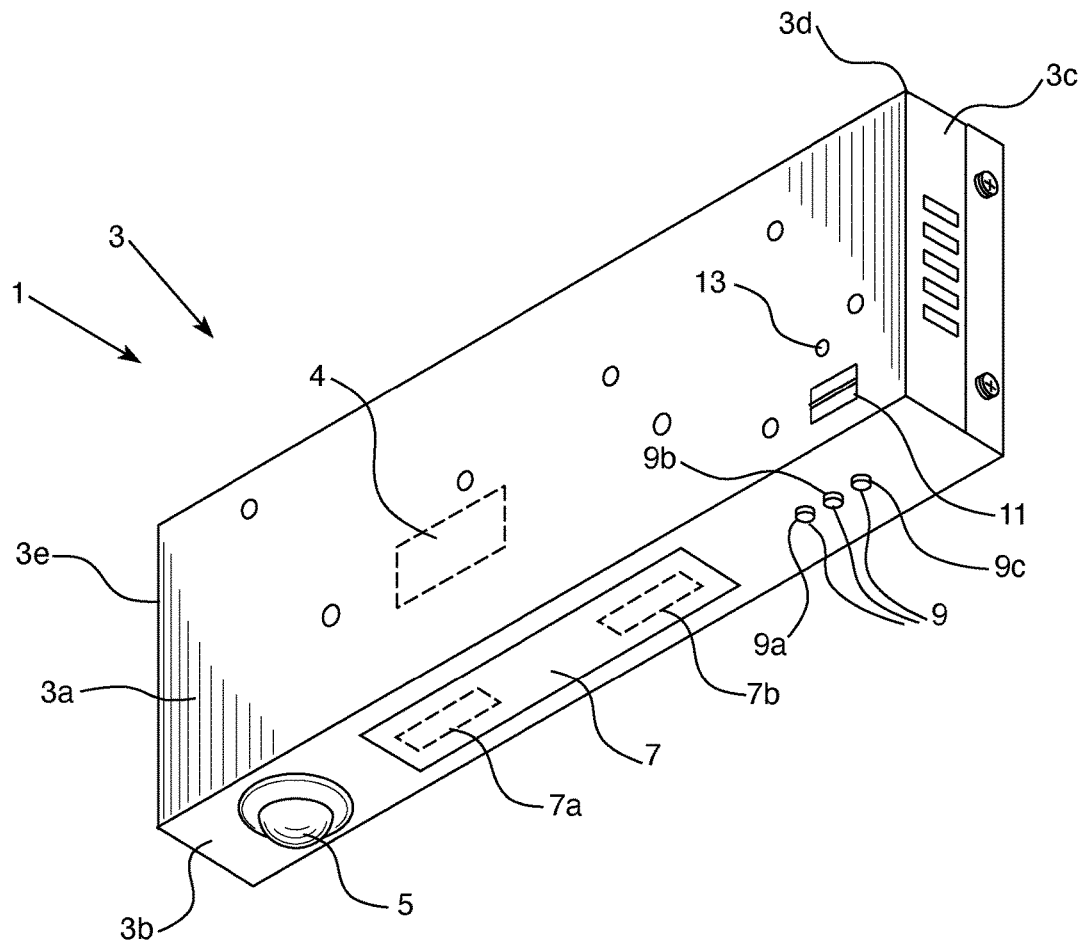
FIG. 1 is a perspective view of a first exemplary embodiment of a disinfection device 1 that can be ceiling mounted within the ceiling of a room of a building, such as the ceiling of a work area WA for providing disinfecting light to one or more pre-defined work spaces WS within the work area WA.
Figure 2:
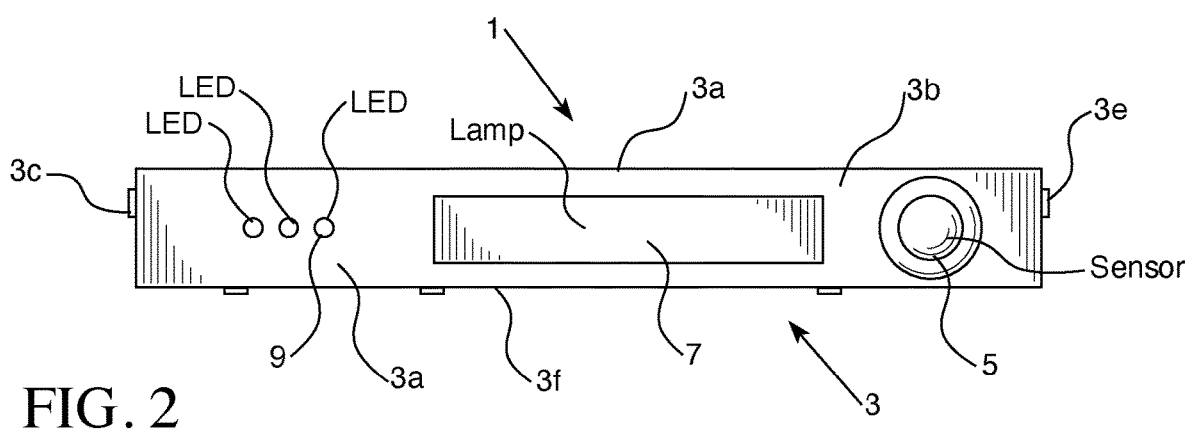
FIG. 2 is a bottom view of the first exemplary embodiment of the disinfection device.

Embodiments of a disinfection device 1 that can be incorporated into a baffle 31, ceiling tile, or other ceiling structure to provide a ceiling mounted disinfection device for disinfection of one or more work spaces WS within a work area WA of an office building or other building. The disinfection device 1 can include a housing 3. The housing 3 can have a first side 3a, a second 3f opposite its first side, a third side 3c and a fourth side 3e that is opposite the third side 3c, a fifth side 3d and a sixth side 3b that is opposite the fifth side 3d. The third side, 3c, fourth side 3e, fifth side 3d, and sixth side 3b can each extend between the first and second sides 3a and 3f. The third side 3c can extend between the fifth side 3d and the sixth side 3b. The fourth side 3e can also extend between the fifth side 3d and sixth side 3b. The sixth side 3b can extend between the third side 3c and the fourth side 3e and the fifth side 3d can extend between the third side 3c and the fourth side 3e. In some embodiments, the housing can be rectangular shaped. In other embodiments, the housing 3 can be shaped as a disc, a plate, have a polygonal shape, have a rounded shape, or have an irregular shape.

The housing 3 can be configured and sized to be mounted to a ceiling mounted baffle, a ceiling, ceiling tile, or other ceiling structure. It can alternatively be configured to be attachable to a pole, beam, privacy screen, partition wall, or other structure so the disinfection device 1 is mounted above the floor of a work area and positioned near a ceiling so that the disinfection device 1 can be positioned above tables, desks, or other work furniture.

The disinfection device 1 can include a sensor 5, a lamp 7, and at least one light emitting diode (LED) 9. For example, there can be a first LED 9a, a second LED 9b, and a third LED 9c. The disinfection device 1 can include a power cord that can be plugged in to an outlet or other electrical connector so that the disinfection device 1 can receive electricity to power the device. The disinfection device 1 can also include a battery backup for powering the device for some period of time in the event the electrical connection fails or there is a power interruption.

Figure 10:
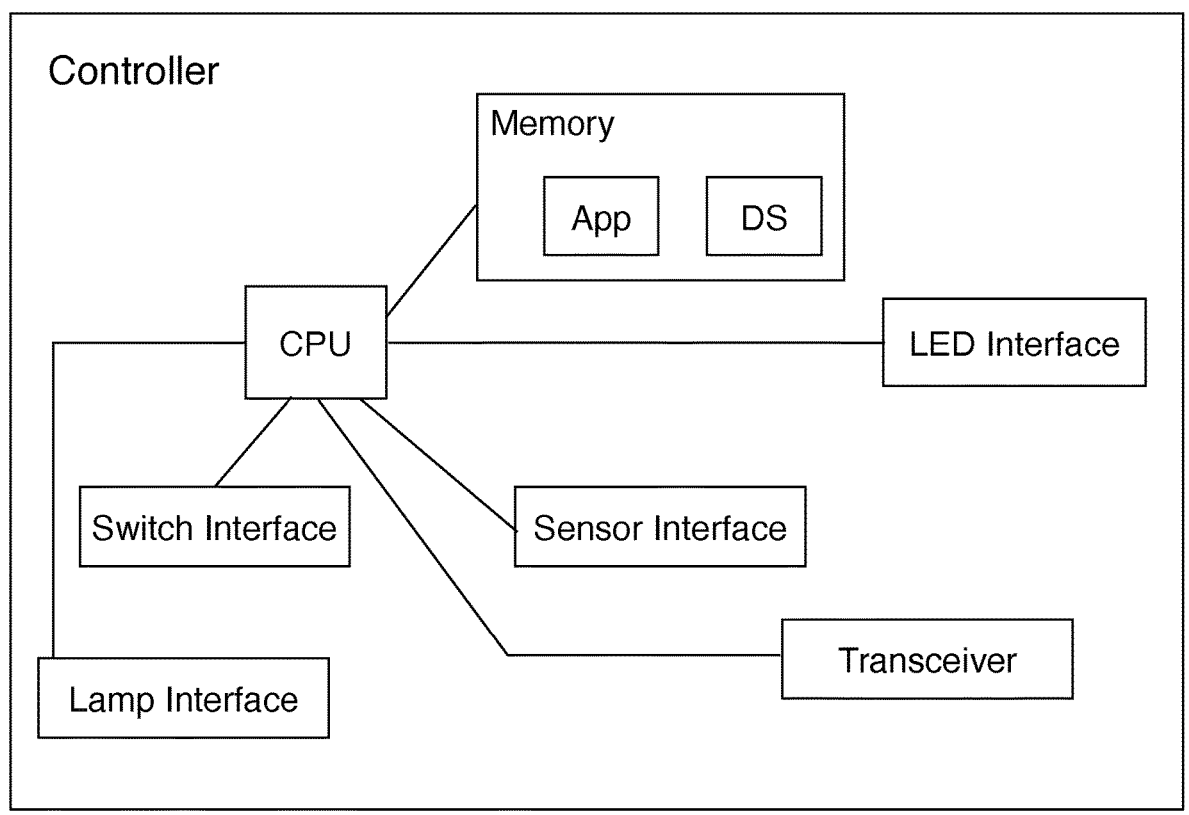
FIG. 10 is a block diagram of an exemplary controller 4 that can be included in the first exemplary embodiment of the disinfection device 1.

Each LED 9 can be positioned in or on the sixth side 3b of the housing 3. The lamp 7 and sensor 5 can also be positioned in or on the sixth side 3b of the housing. The sensor 5 can be a motion sensor or other type of sensor configured to detect motion of an object (e.g. person, animal, etc.) within the field of the sensor to automatically turn on a first light emission device 7a of the lamp 7 in response to detection of the motion. A controller 4 (shown in broken line in FIG. 1 and also illustrated in FIG. 10) can be communicatively connected to the sensor 5 and to the lamp 7 to control the turning on of the first light emission device 7a of the lamp in response to the sensor 5 detecting motion within a work space WS or work area WA. The controller 4 can also be configured to automatically turn the first light emission device 7a off if the sensor 5 fails to detect motion within a pre-selected work space illumination time period after the first light emission device 7a is turned on to output visible light toward the work space WS.

The disinfection device 1 can also include a second light emission device 7b of the lamp 7. The second light emission device 7b can be structured as an excimer lamp or an excilamp in some embodiments. The second light emission device 7b can also be considered an ultraviolet (UV) light emission device 7b.

The second light emission device 7b can be configured to emit an ultraviolet (UV) light that is not visible to human eyesight (e.g. UV light that has a wavelength of between 100-400 nanometers (nm)). The UV light emitted by the second light emission device 7b can have a wavelength of between 200-280 nm and be within a UVC classification of UV light. For example, the UV light emitted by the second light emission device can have a wavelength of 222 nm and be classified as UVC light in some embodiments. The UVC light emission can be considered safer to humans as compared to other types of UV light (e.g. UV light having a wavelength of over 280 nm and less than 400 nm). In some embodiments, the second light emission device 7b can be configured to emit a UVC light that is between 225 nm and 200 nm in wavelength or is 222 nm in wavelength as such wavelengths of UVC light may be prevented from passing through an outer stratum corneum of a human epidermis layer (e.g. skin) as compared to UVC light having a wavelength of over 250 nm, which can pass into the stratum spinosum layer of the human epidermis, which is between the stratum granulosum and stratum basale layers of the human epidermis. Such a UVC light having a wavelength that is no more than 225 nm and is not less than 200 nm also can be less harmful to human eyes as such light is unable to pass through the cornea to the aqueous humor layer of the eye. In contrast, UV light having a wavelength of over 250 nm (e.g. a wavelength of 254 nm) can pass through the cornea and into the aqueous humor layer of the human eye.

In some embodiments, the lamp 7 can be configured so it only provides a disinfection light and does not provide any type of visible illumination. In such embodiments, the disinfection device 1 may not include the first light emission device 7a. In such embodiments, the second light emission device 7b can be considered a first light emission device. For example, the lamp 7 can be structured as an excilamp or an eximer lamp in such embodiments.

The controller 4 can include a processor CPU that is communicatively connected to a non-transitory computer readable medium such as a non-transitory memory or flash memory. The memory can store at least one application App and at least one data store DS. The data store DS can include at least one database, at least one file, or other type of data store. The processor CPU can also be communicatively connected to a lamp interface for communications with the first and second light emission devices 7b of the lamp 7 or for communication with the lamp 7 for controlling operation of the lamp 7 and each of its light emission devices (e.g. just the second light emission device 7b when just that device is included as a first light emission device, or both the first and second light emissions devices 7a and 7b when both are included, etc.). The processor CPU can also be communicatively connected to a mode switch 13 for receipt of input to indicate which operational mode the controller 4 is to operate in, a sensor interface for communications with the sensor 5 to receive data concerning any detection of motion and/or lack of a detection of motion by the sensor 5, an LED interface for actuating the illumination or non-illumination of each of the LEDs 9, and a transceiver for communication with one or more other elements of the disinfection device or a remote device. For instance, the transceiver can include a Bluetooth transceiver or a Wi-Fi transceiver for wireless communication with a computer device of a user (e.g. smart phone, laptop computer, tablet device, etc.) to provide data to the user and/or to receive input or other data from a user for control of operation of the controller, updating of software of the controller, or communicating a log of activity related to operations of the disinfection device 1 (e.g. a log of disinfection activities and/or a log of detections of vacancy time periods in a work area WA and/or non-vacancy time periods in the work area WA).

The processor CPU of the controller 4 can control operations of the disinfection device 1 by running a control program defined by code of an application App. The particular mode of operation that is run can be based on a default setting or based on input received via the mode switch 13. The controller 4 can provide control signals to the LEDs 9 for illumination of the LEDs, and provide control signals or other data to the lamp 7 and/or the light emission devices of the lamp 7 via the lamp interface and LED interface to which the processor CPU is connected. The transmission of such control signals can be based on data received from the sensor 5 via the sensor interface and based on the operational mode that the controller 4 is operating in, which can be adjusted via the mode switch 11 and its connection to the processor CPU via the controller's switch interface, for example.

It should be appreciated that the controller 4 includes hardware elements for controlling operations of the disinfection device and can be powered via electricity received from a connection the controller 4 has to an electrical outlet to which a power cord of the disinfection device is connectable and/or a battery of the disinfection device 1. In other embodiments, the controller 4 can have other designs and can include other circuitry or other hardware elements.

Figure 3:
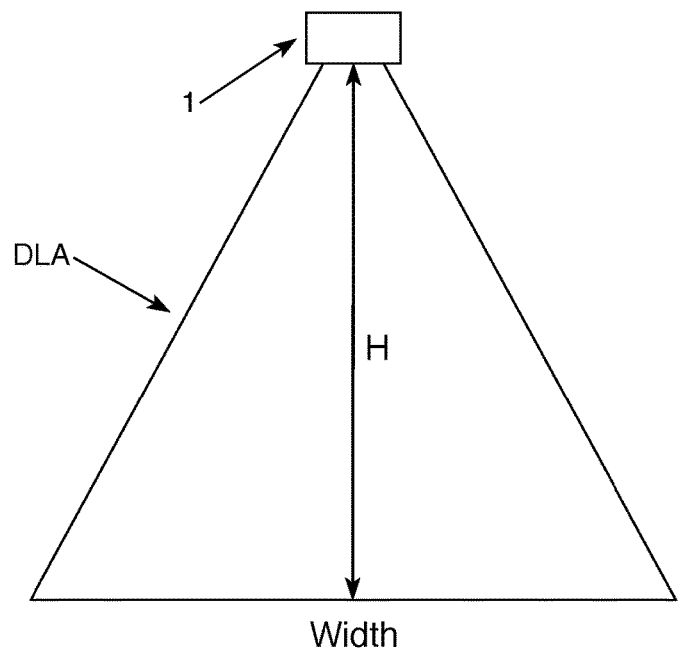
FIG. 3 is a schematic view of the first exemplary embodiment of the disinfection device mounted to a ceiling to emit disinfecting light within a distribution of light area DLA.
Figure 4:
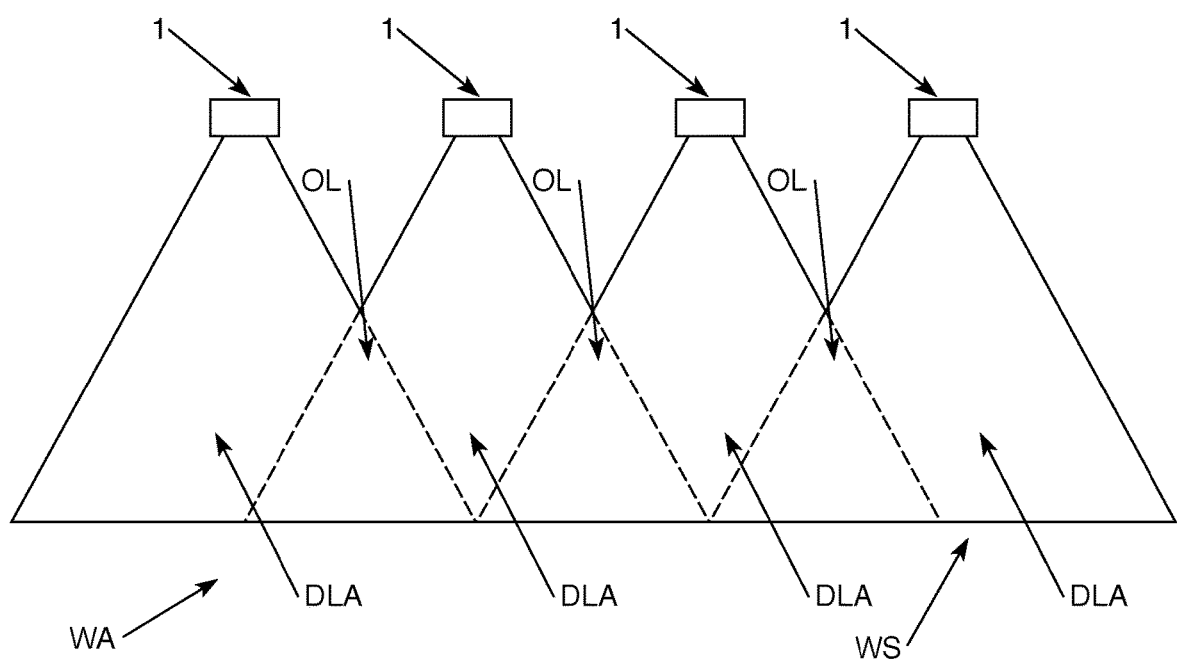
FIG. 4 is a schematic view of an array of the first exemplary embodiment of the disinfection devices mounted to a ceiling to emit disinfecting light within overlapping disinfecting light areas.

As may best be seen from FIGS. 3 and 4, the lamp 7 can be configured so that the second light emission device 7b emits a UV light (e.g. a UVC light such as, for example, a UVC-222 light) in a distribution of light area DLA that can have a height H between the lamp 7 and the floor of an office or other work area WA. In some embodiments, the height can be seven feet (2.1336 meters (m)), more than seven feet, or less than seven feet. For example, the height H can be less than or equal to 12 feet (3.6576 m), less than or equal to 10 feet (3.05 m), less than 3 m, 8 feet or less, 6.6 feet (2 m) or 3.3 feet (1 m). The height H can also be greater than at least 0.5 meters, or 1.5 feet for some embodiments.

The width of the distribution of light area DLA can be fourteen feet, (14.267 m) less than fourteen feet, or more than fourteen feet. The width of the distribution of light area can extend in multiple directions (e.g. the width of the distribution of light area can be a diameter of the distribution of light are DLA) to define a surface area and a volume of light that is provided by the UV light emitted by the second light emission device 7b of the lamp 7.

Figure 5:
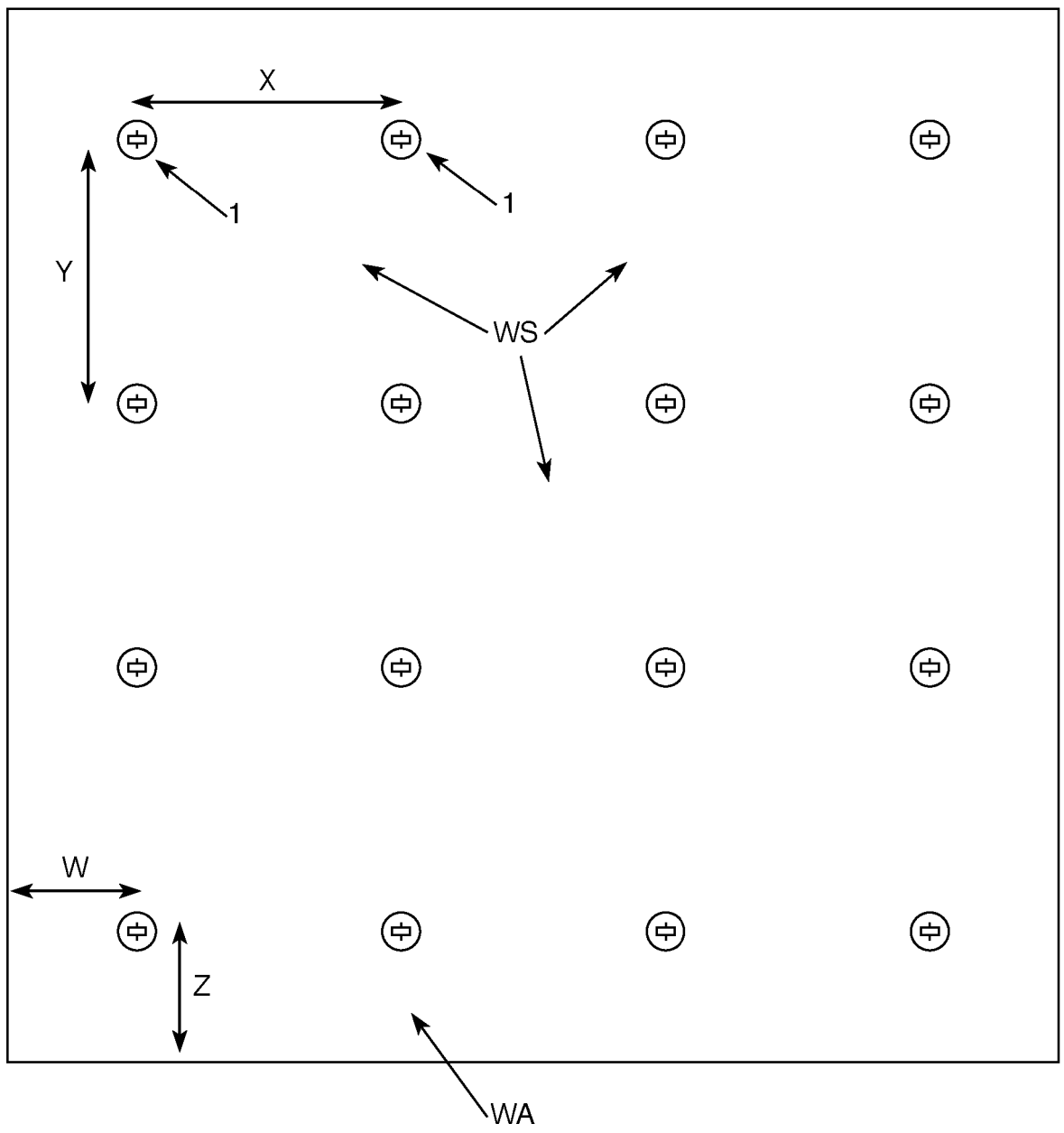
FIG. 5 is a schematic view of a first exemplary arrangement of disinfection devices positioned in or on a ceiling of a work area WA for providing disinfecting light to a plurality of work spaces WS within the work area WA.
Figure 7:
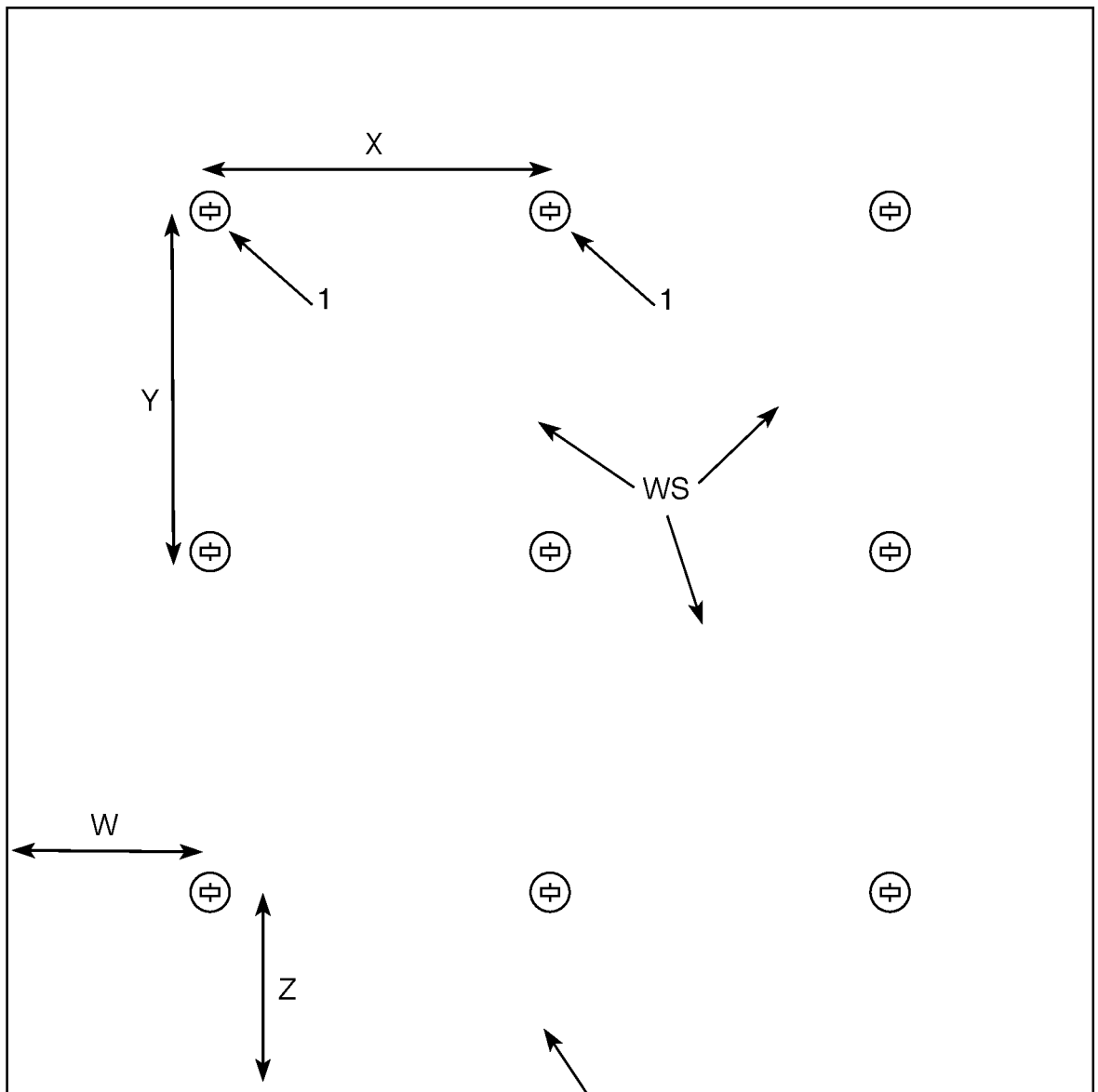
FIG. 7 is a schematic view of a second exemplary arrangement of disinfection devices positioned in or on a ceiling of a work area WA for providing disinfecting light to a plurality of work spaces WS within the work area WA.

FIGS. 5 and 7 illustrate different exemplary arrangements of disinfection devices 1 that can be provided in a work area WA to provide a distribution of light areas therein to provide UV light to multiple work spaces WS within the work area WA. For instance, each work space WS can be a cubicle or a particular pre-defined area within an office building at which UV light emitted by the disinfection device 1 can be output. Each work space WS can have one or more desks or tables, one or more chairs, as well as other furniture and equipment (e.g. phones, computers, privacy screens, tack boards, etc.). The disinfection devices 1 can be positioned so the UV light emitted via their lamps 7 is directed onto this furniture and/or other equipment in each lamp's particular distribution of light area DLA within each work space WS.

Multiple disinfection devices 1 can be spaced apart from each other and aligned so that their distribution of light areas DLAs overlap in overlap regions OL to help ensure adequate coverage of a particular work space WS or work area WA. In other embodiments, the disinfection devices 1 can be spaced so that there is minimal to no overlapping of distribution of light areas DLAs.

Referring to FIG. 5, a first arrangement of disinfection devices 1 can include a series of rows of disinfection devices and a series of columns of disinfection devices 1. Each row can include a number of disinfection devices 1 that are each spaced apart from each other by a first row distance X. Each column can include a number of disinfection devices 1 that are each spaced apart from each other by a first column distance Y. The peripheral rows and columns of the disinfection devices 1 can be spaced apart from any walls of a room defining the work area WA. Each disinfection device 1 of a peripheral row can be spaced apart from a wall by a first wall distance Z and each distribution device 1 of a peripheral column can be spaced apart from a wall of the work area WA by a second wall distance W.

Figure 6:
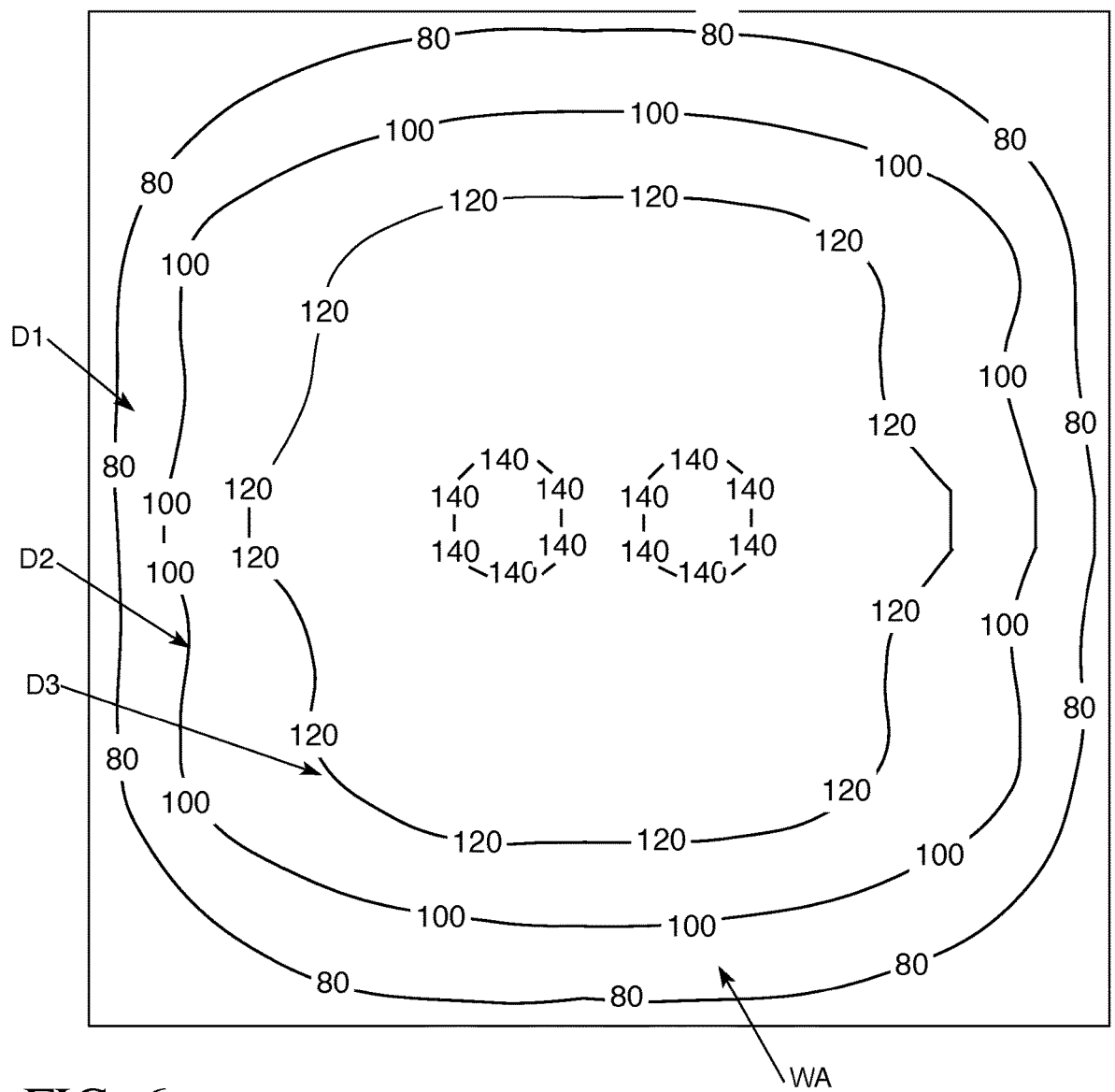
FIG. 6 is a schematic view of an exemplary irradiance distribution for the first exemplary arrangement of disinfection devices illustrated in FIG. 4.

FIG. 6 illustrates an exemplary irradiance distribution on a table that is at a height of 2.5 feet (0.762 m) in which there is 10 feet (3.05 m) from the tabletop to the ceiling position of the lamps of the disinfection devices 1 for a table in a work space WS of the arrangement of FIG. 5 in which the disinfection devices 1 are mounted in or on the ceiling so that each one is 12.5 feet (3.81 m) above the floor of the work area WA, the first row distance X is 8 feet (2.44 m), the first column distance Y is 8 feet (2.44 m), the first wall distance Z is 4 feet (1.22 m) and the second wall distance W is 4 feet (1.22 m). The area of the work area WA is 32 feet (9.7536 m) by 32 feet (9.7536 m), which is 1,024 ft$^2$ (95.1 m$^2$). An emission of UVC light to provide a dose of at least 6 milliJoules per square centimeter (mJ/cm$^2$) to the tabletop can be applied by the disinfection devices 1 within a disinfection time period. As shown in FIG. 6, a first dose D1 at isoline 80 required 125 minutes for a UVC light emission of 222 nm to provide a dose that can provide a disinfection of 99.9% of SARS-CoV-2 (COVID-19) virus on the tabletop. A second dose D2 at isoline 100 required 100 minutes of exposure to the UVC light emission of 222 nm to provide a dose for disinfection of 99.9% the COVID-19 virus on the tabletop. A third dose D3 at isoline 120 required 83 minutes of exposure to the UVC light emission of 222 nm to provide a dose for a disinfection of 99.9% of the COVID-19 virus on the tabletop. Isoline 140 in FIG. 6 required less than 83 minutes of exposure to provide a dose that would provide a disinfection of 99.9% of the COVID-19 virus on the tabletop.

Referring to FIG. 7, a second arrangement of disinfection devices 1 can include a series of rows of disinfection devices and a series of columns of disinfection devices 1. Each row can include a number of disinfection devices 1 that are each spaced apart from each other by a second row distance X. Each column can include a number of disinfection devices 1 that are each spaced apart from each other by a second column distance Y. The peripheral rows and columns of the disinfection devices 1 can be spaced apart from any walls of a room defining the work area WA. Each disinfection device 1 of a peripheral row can be spaced apart from a wall by a first wall distance Z and each distribution device 1 of a peripheral column can be spaced apart from a wall of the work area WA by a second wall distance W.

Figure 8:
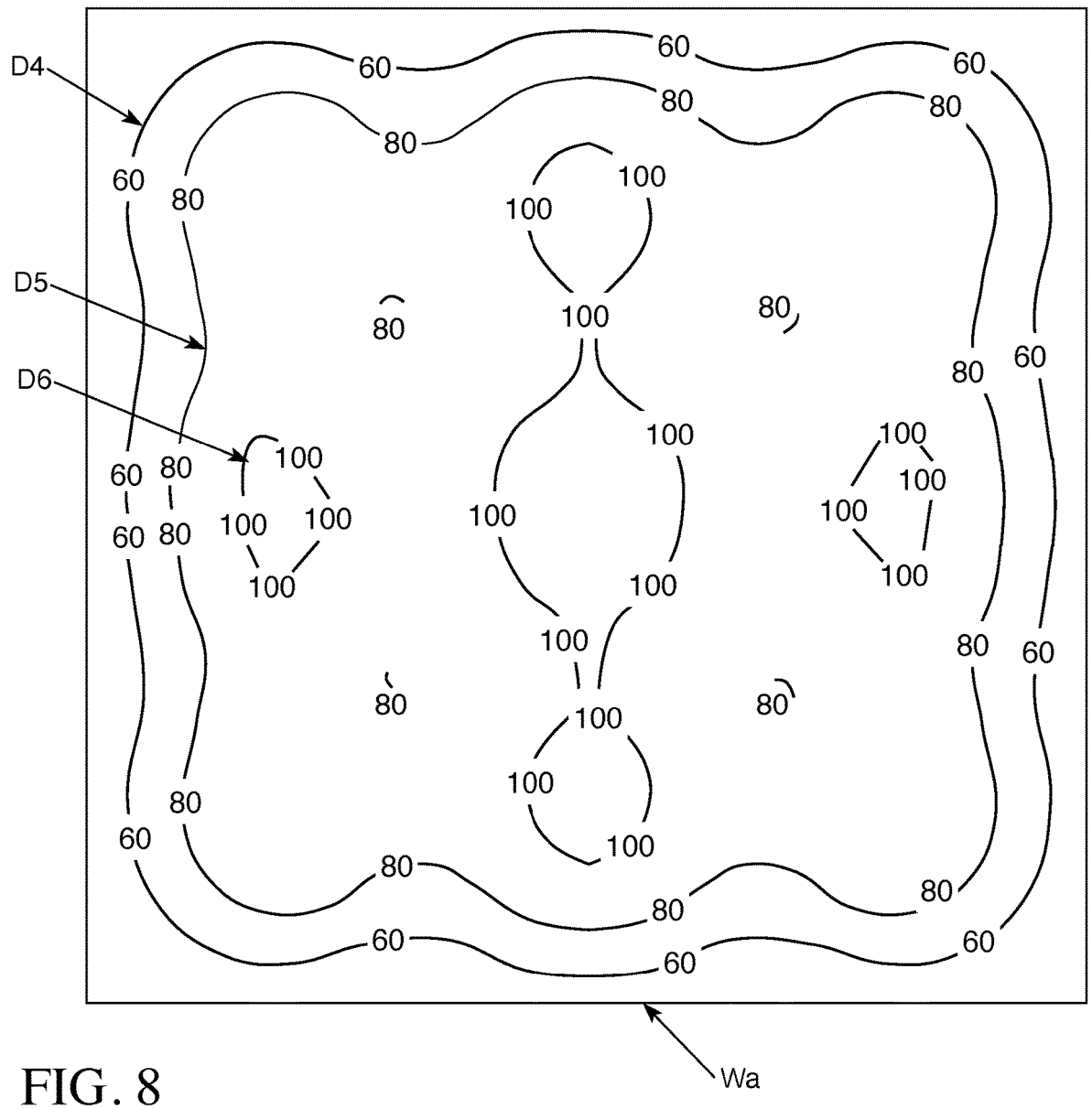
FIG. 8 is a schematic view of an exemplary irradiance distribution for the second exemplary arrangement of disinfection devices illustrated in FIG. 6.

FIG. 8 illustrates an exemplary irradiance distribution on a table in a work space WS that is at a height of 0.75 meters in which there is a distance of 2 meters from the tabletop to the ceiling position of the lamps of the disinfection devices 1 for the arrangement of FIG. 7 in which the disinfection devices 1 are mounted in or on the ceiling so that each one is 2.75 meters above the floor of the work area WA, the second row distance X is 3 meters, the second column distance Y is 3 meters, the first wall distance Z is 1.8 meters and the second wall distance W is 1.8 meters. The overall area of the work area WA is 9.6 meters by 9.6 meters (e.g. 19.2 m$^2$ area). An emission of UVC light to provide a dose of at least 6 mJ/cm$^2$ to the tabletop can be applied by the disinfection devices 1 within a disinfection time period. As shown in FIG. 8, a first dose D4 at isoline 60 in FIG. 8 required 167 minutes for a UVC light emission of 222 nm to provide a dose that can provide a disinfection of 99.9% of COVID-19 virus on the tabletop. A second dose D5 at isoline 80 in FIG. 8 required 125 minutes of exposure to the UVC light emission of 222 nm to provide a dose for disinfection of 99.9% of the COVID-19 virus on the tabletop. A third dose D6 at isoline 100 in FIG. 8 required 100 minutes of exposure to the UVC light emission of 222 nm to provide a dose for a disinfection of 99.9% of the COVID-19 virus on the tabletop.

Figure 9:
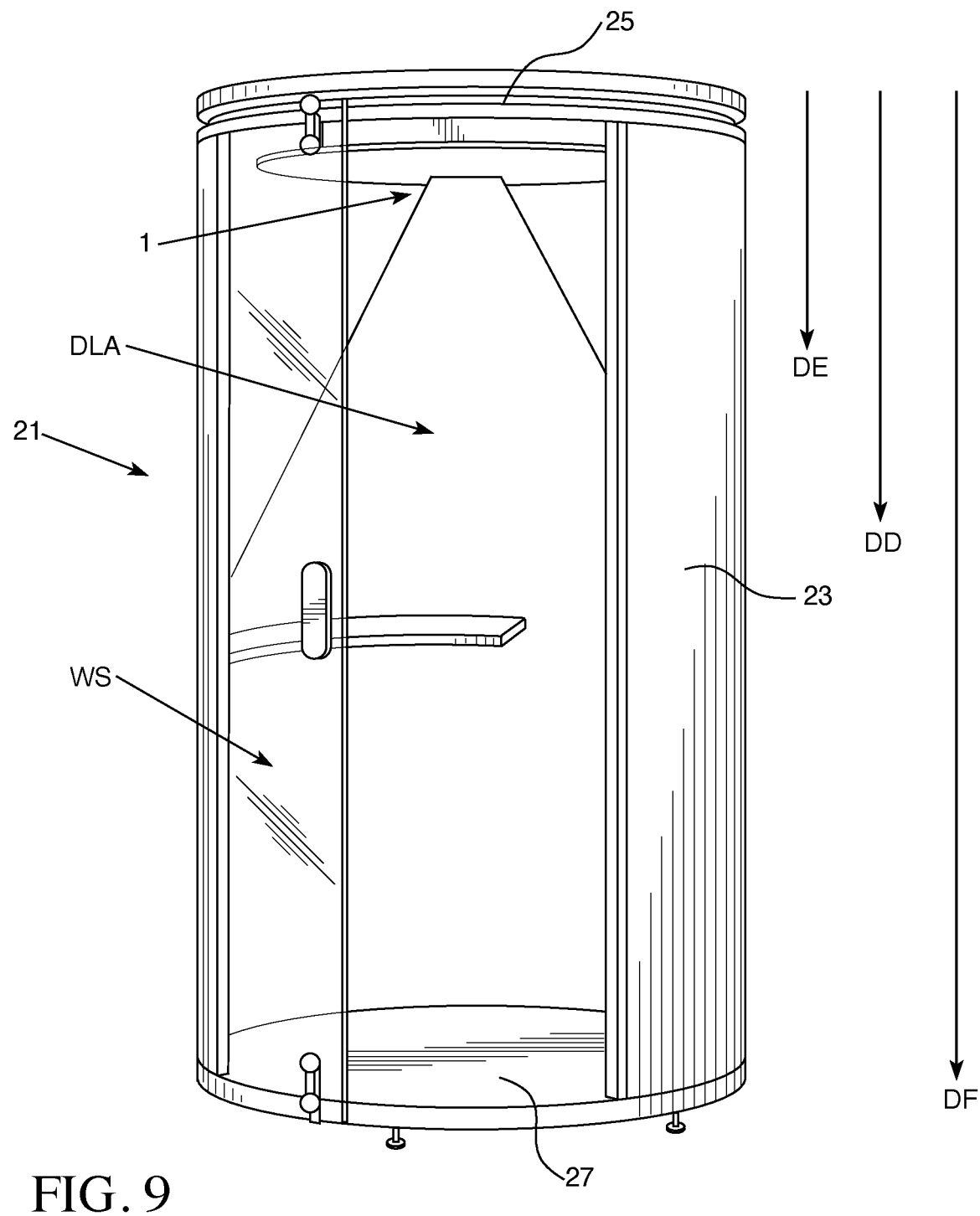
FIG. 9 is a perspective view of an exemplary embodiment of a privacy booth that is positionable within a work area WA that can include the first exemplary embodiment of the disinfection device 1.

Embodiments of the disinfection device 1 can be incorporated into furniture or partition structures. For instance, a privacy booth structure 21 that can be positionable in a work area WA or within an office building can include an outer housing that has a ceiling 25, a floor 27, and at least one sidewall 23 that extends between the floor 27 and the ceiling 25 of the privacy booth structure 21. There can also be a door for opening and closing an interior work space WS defined between the floor 27, ceiling 25 and at least one sidewall 23. At least one disinfection device 1 can be positioned in or on the ceiling 25 or mounted to the ceiling 25 to emit light within a distribution of light area DLA inside the defined work space WS. The disinfection device 1 can be mounted to the ceiling 25 within the work space WS, for example. In some embodiments, the lamp 7 of the disinfection device can be positioned to provide an irradiance dose via emission of a UVC light having a wavelength of between 250 nm and 200 nm or between 225 nm and 200 nm within a pre-selected disinfection time that can depend on how far away a portion of the sidewall 23 or floor 27 is from the lamp 7. Table 1 below provides the irradiance, center disinfection time, and edge disinfection time for distances DE, DD, and DF shown in FIG. 9, in which the distance DE is 32 inches (81.3 centimeters (cm)) from the lamp 7, distance DD is 51 inches (129.54 cm) from the lamp 7, and the floor 27 is 79 inches (200.66 cm) from the lamp where the lamp emits UVC light at a 222 nm wavelength. If should be understood that other embodiments can have other distances for the distanced DE, DD, and DF based on a particular design or geometry of the privacy booth structure 21.

TABLE 1

Dose of 6mJ/cm$^2$ to provide disinfection for 99.9% of the COVID virus

| Distance from lamp | Irradiance (μW/cm$^2$) | Disinfection time, center (min) | Disinfection time, edge (min) |
|---|---|---|---|
| DE (32 inches) | 6.1 | 16 | 32 |
| DD (51 inches) | 2.3 | 43 | 59 |
| DF (79 inches) | 0.97 | 103 | 112 |

The disinfection device 1 can be employed to facilitate ease of use and ease of maintenance. For instance, the first LED 9a can be configured to illuminate in a first color (e.g. green) to indicate that the disinfection device is powered on and ready for operation (e.g. is receiving electricity from an outlet or sufficiently powered battery). The second LED 9b can be illuminable in a second color (e.g. purple) to indicate that the lamp 7 is activated so that the second light emission device 7b is activated and non-visible UV light is being output from the lamp 7 to disinfect a work space WS and/or work area WA. The third LED 9c can be illuminable in a third color (e.g. red) in response to detecting that the UV emission tube for the second light emission device 7b has expired and needs replaced. The third LED can be configured to repeatedly blink in the third color in response to detection of a low level of life of the UV tube (e.g. the UV tube is determined to be within a pre-selected low threshold of life to indicate the UV tube will need replaced relatively soon). The controller 4 can be connected to the LEDs 9 via the LED interface to control the illumination and/or blinking of the LEDs 9 in response to such parameters.

The disinfection device 1 can also include a mode switch 13 and a mode indicator 11. The mode switch 13 can be connected to the controller 4 and is moveable between different positions to change operation of the disinfection device between multiple different operational modes defined in code stored in non-transitory memory that is connected to a processor CPU of the controller 4 to define operational modes for the disinfection device 1. The controller 4 can be connected to a mode indicator 11 via a mode indicator interface. The mode indicator can be configured to emit output (e.g. display a light of a particular color or light in a particular number or provide other indicia) to indicate which mode the disinfection device is in or whether the mode is not properly set and corrective action is needed to correct the mode of the disinfection device 1. The display or other indicia provided by the mode indicator 11 can be based on data or control signals that it receives from the processor CPU of the controller 4 to which it is communicatively connected via the mode indicator interface.

In a first mode, the disinfection device 1 can be configured so that the sensor 5 is enabled to detect when a work space WS or work area WA is vacant to actuate an automatic application of UV light to a work space WS or work area WA. For example, when a lack of motion is detected for a pre-selected vacancy time period (e.g. 3 minutes of no motion, 5 minutes of no motion, 10 minutes of no motion, etc.), the controller can be configured to activate the lamp 7 so that the second light emission device 7b is activated to provide UV light to a distribution of light area DLA within the work space WS or work area WA for a pre-selected disinfection time period (e.g. 20 minutes, 100 minutes, 120 minutes, 140 minutes, 160 minutes, 180 minutes, no more than three hours, no more than two hours, no more than 1 hour, no more than 30 minutes, etc.).

In some embodiments, the actuation of the UV light can occur at the same time that deactivation of visible light is to occur so that the UV light is applied while visible light is not output from the first light emission device 7a of the lamp 7. In other embodiments, the deactivation of the first light emission device 7a can be independent of the activation of the second light emission device 7b.

After the UV light is actuated for disinfection, the controller 4 can be configured so that in response to the sensor 5 detecting occupant motion while the second light emission device 7b is actively emitting UV light, the controller 4 will turn the second light emission device 7b and/or lamp 7 off to stop output of the UV light and interrupt the disinfection cycle. In embodiments that utilize the first light emission device 7a, the detection of motion can also trigger actuation of the first light emission device 7a so that visible light is output from the lamp 7.

In a first mode, in the event the disinfection cycle is interrupted, the controller 4 can have it resumed where it left off in response to no occupant motion being detected for the pre-selected vacancy time that may occur after interruption (e.g. if the disinfection was interrupted at minute 10 of a twenty minute cycle, the emission of UV light will resume for another 10 minutes after vacancy is again detected). The running time for disinfection in such a mode can be tracked by the controller so that multiple stoppages due to detected motion are accounted for and the resumption of UV light emissions occurs so that the UV light is emitted for an entirety of the pre-selected disinfection timer period in spite of being stopped due to detection motion one or more times during the cleaning cycle. In a second operational mode, the controller 4 can be configured so that, in the event the disinfection cycle is interrupted via detected motion, the disinfection cycle will restart to apply the UV light for the entirety of the pre-selected disinfection time period in response to no occupant motion being detected for the pre-selected vacancy time after the disinfection cycle was interrupted.

In yet a third mode, the controller 4 can be configured so that the disinfection device 1 applies UV light for the pre-selected disinfection time period at a pre-selected time each day or on particular days of the week. The controller 4 can be configured so that, in response to detection of motion in the work space WS via the sensor 5, the application of UV light is halted. The disinfection cycle can then resume where it left off in response to no occupant motion being detected for the pre-selected vacancy time that may occur after interruption after the disinfection cycle was interrupted.

In yet a fourth mode, the controller 4 can be configured so that the disinfection device 1 applies UV light for the pre-selected disinfection time period at a pre-selected time each day or on particular days of the week. The controller 4 can be configured so that, in response to detection of motion in the work space WS via the sensor 5, the application of UV light is halted. The disinfection cycle can then restart to apply the UV light for the entirety of the pre-selected disinfection time period in response to no occupant motion being detected for the pre-selected vacancy time.

In the third and fourth modes of operation, the time for the disinfection cycle can be selected so that it is a time that the work area would be expected to be vacant. For instance, a time in the midnight to 4 AM time period, or the 10 PM to 4 AM time period could be selected. As another example, a time range on a weekend day or holiday day can be selected.

It should be appreciated that the controller 4 of the disinfection device can be configured to provide one or more modes of operation for different embodiments. For instance, the controller 4 of the disinfection device can be configured to provide a single mode of operation, only two modes of operation, only three modes of operation, four modes of operation, or more than four modes of operation for different embodiments to meet different design criteria and/or operational criteria.

Figure 11:
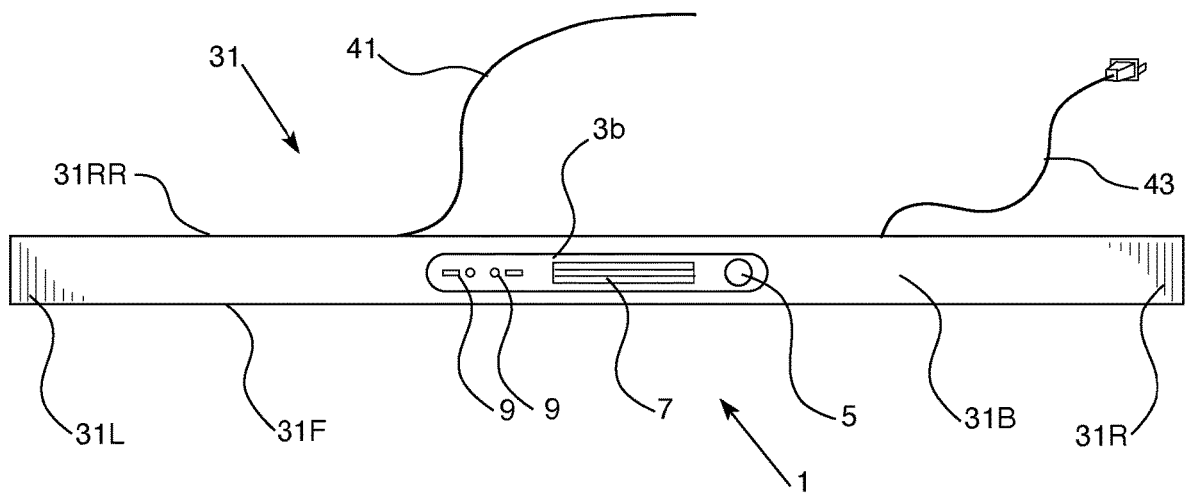
FIG. 11 is a perspective view of a first exemplary embodiment of a baffle 31 having the first exemplary embodiment of the disinfection device 1.
Figure 12:
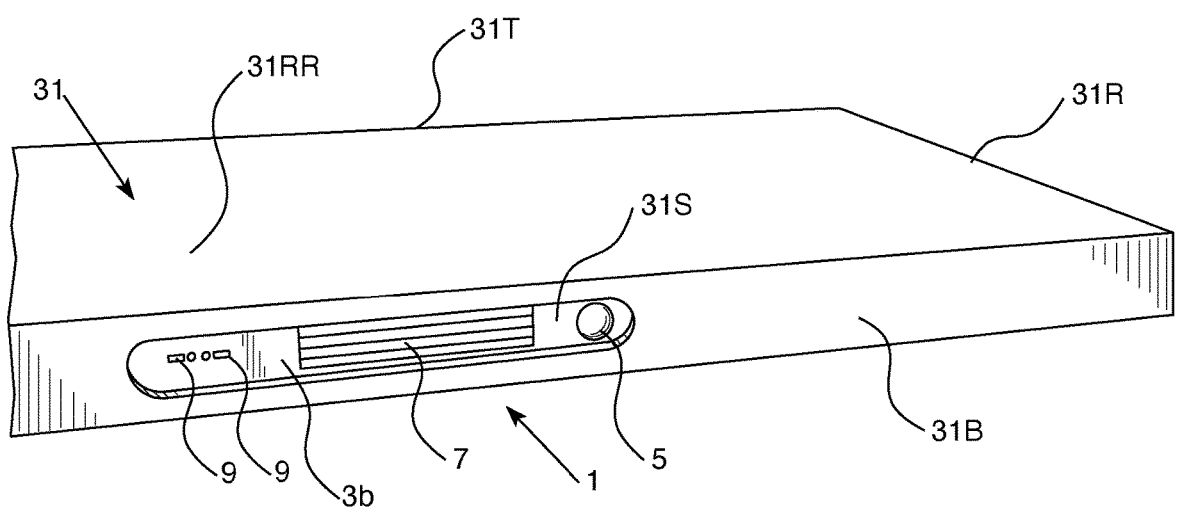
FIG. 12 is another perspective view of the first exemplary embodiment of a baffle 31 having the first exemplary embodiment of the disinfection device 1.

The disinfection device 1 can be positionable in a baffle 31 or a ceiling tile to be positionable above a work area WA or work space WS for illuminating that area or space with UV light as well as other light as discussed herein. FIGS. 11-12 illustrate one example configuration of a baffle 31 that utilizes the disinfection device. Of course, other baffle configurations can also be utilized or a ceiling tile configuration can alternatively be utilized for positioning of the disinfection device 1.

As can be appreciated from FIGS. 11-12, the baffle 31 can include an outer housing having a left side 31L, a right side 31R, a rear side 31RR, a front side 31F, a bottom side 31B and a top side 31T. The top side 31T can be opposite the bottom side 31B, the left side 31L and can be opposite the right side 31R and the front side 31F can be opposite the rear side 31RR.

The bottom side 31B can have a slot 31S defined therein for receipt of the disinfection device 1 and/or for providing a space that the sensor 5, LEDs 9, and lamp 7 can be exposed for a user to view those elements as well as permitting the sensor 5 to function, the LED illumination to be seen, and the lamp 7 to be able to emit UV light or other light toward a work space WS or work area WA. The mode switch 13 and mode indicator 11 can also be positioned on the bottom side 31B so that these elements are viewable through the slot 31S so they can also be seen by a user as well. In other embodiments, the front, back, left, or right sides can have a slot aligned with a position of where the mode switch 13 and mode indicator 11 are positioned so that they can be seen by a user while the baffle 31 is mounted above a work area WA (e.g. mounted to a ceiling, positioned adjacent a ceiling, etc.). The disinfection device 1 can be positioned within a cavity of the baffle 31 defined by its top, bottom, left, right, front, and rear sides that is in communication with the slot 31S for positioning of the disinfection device within the baffle 31 for mounting of the disinfection device via the mounting device(s) 41 of the baffle.

The baffle 31 can be configured so that one or more mounting devices 41 can be connected to the baffle 31 to hang the baffle from a ceiling or other structure. Each mounting device can include a cable or wire that may extend from the baffle for attachment to the ceiling or other structure of a building to position the baffle over furniture in a work space WS of a work area WA. The baffle 31 can also include a channel and/or hole that permits a power cord 43 of the disinfection device to extend out of the baffle 31 to be plugged into an outlet or an extension cord or other power cord transmission connector for providing electricity to the disinfection device 1. The hole and/or channel can be in the top side 31T to help permit the power cord to extend out of the baffle or permit an extension cord or other electricity transmission line to extend into the baffle or coupling to the disinfection device 1 for powering that device.

The outer sides of the baffle can be composed of a material that can help absorb sound. For instance, the outer sides of the baffle 31 can be composed of felt or other material that can help absorb sound to help provide a quieting effect for the work area WA or work space WS in addition to providing the disinfection function provided by the disinfection device 1. These outer sides of the baffle can define a covering or partial covering that covers the disinfection device 1 positioned within the covering. The shape of the baffle 31 can be rectangular as shown in FIGS. 11-12. The shape can alternatively be hexagonal, pentagonal, circular, oval, or other shape to provide a desired aesthetic effect.

Figure 13:
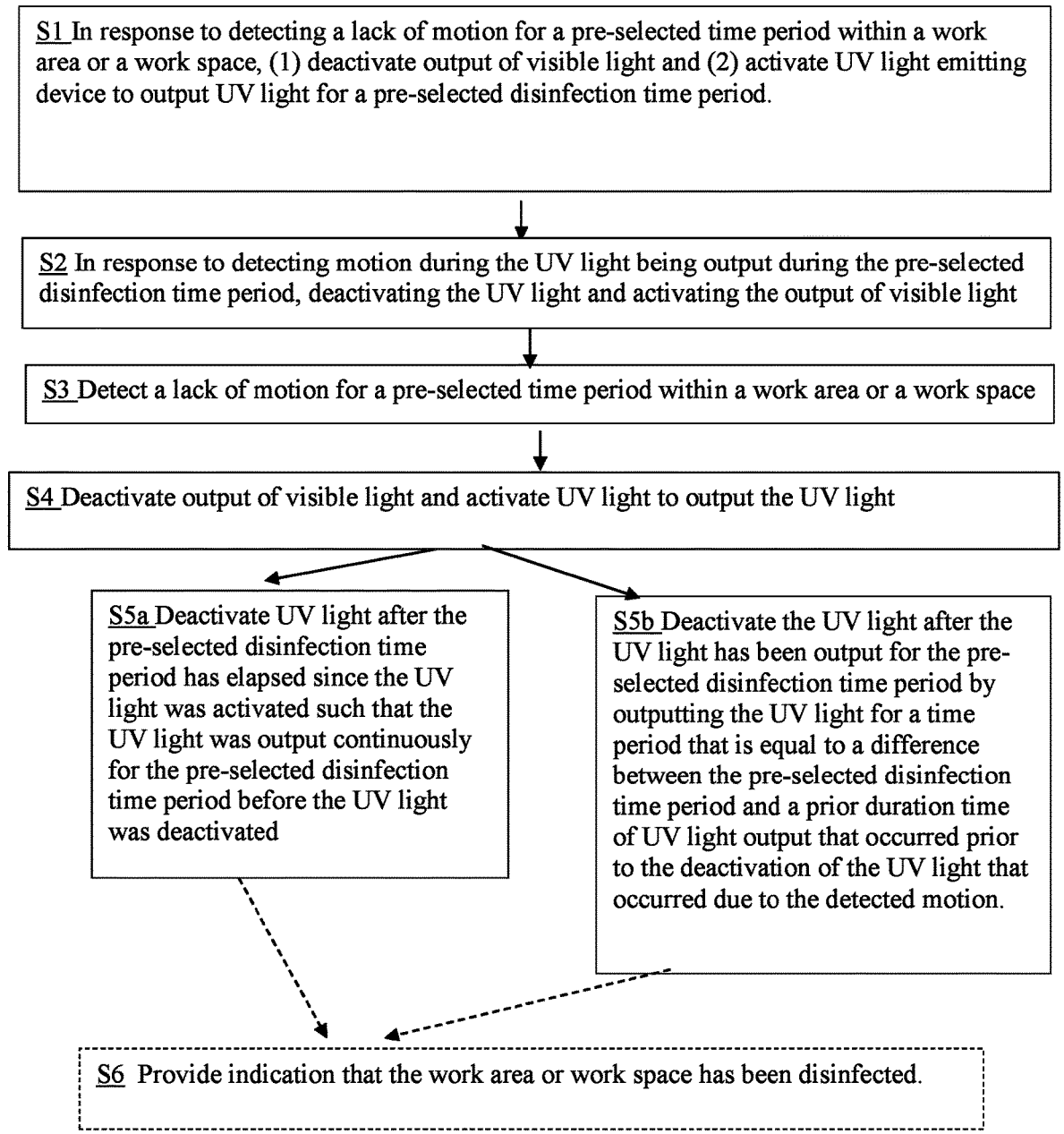
FIG. 13 is a flow chart illustrating an exemplary disinfection method for a work area WA for providing disinfecting light to a plurality of work spaces WS within the work area WA for a pre-selected disinfection time period to provide at least a pre-selected disinfection dose to the work area WA.

Embodiments of the disinfection device 1 can be utilized in embodiments of a process for disinfection of a work area or one or more work spaces within a work area. An exemplary embodiment of such a process is shown in FIG. 13, for example. Embodiments of the process can include a first step S1 so that, in response to detecting a lack of motion for a pre-selected time period (e.g. a pre-selected vacancy time period) within the work area WA or a work space WS, output of visible light is deactivated and a UV light emitting device (e.g. UV light emission device 7b) is activated to output UV light for a pre-selected disinfection time period. In some embodiments of the process, the UV light can be emitted continuously for the entirety of the pre-selected disinfection time period. The dose of UV light that is applied can be relatively low so that the pre-selected disinfection time period is at least 60 minutes, at least 70 minutes, or at least 80 minutes in time and can range from 60 minutes to 120 minutes in duration, 60 minutes to 180 minutes in duration or from 60 minutes to 240 minutes duration. If no motion is detected in the work area WA or work space WS, then the UV light can be continuously emitted for the entirety of the pre-selected disinfection time period. Thereafter, the disinfection process can be completed. In some embodiments, an LED 9 or other indicator may be output via the disinfection device to indicate that the work area or work space was disinfected or to indicate that the disinfection cycle was successfully completed.

In some embodiments, the first step S1 may not be performed unless the detection of the lack of motion occurs during a pre-selected disinfection cycle time period. This time period can be set so that the disinfection cycle is expected to be run at a time when a work area or work space is anticipated as having no occupancy or very low occupancy. For example, the disinfection cycle time period can be set as a time that is within 10 PM and 2 AM, between 9 PM and 1 AM, between 9 PM and 4 AM, or another suitable time range that accounts for anticipated occupancy of the work spaces or work area. The controller of the disinfection device can be configured to receive user input for at least one input device (e.g. button, wireless communication connection to a smart phone or laptop, etc.) to allow this disinfection cycle time period to be set by a user or to be adjusted by a user.

In the event motion is detected during the UV light being emitted, a second step S2 of the process can include deactivating the UV light and activating the output of visible light in response to detecting the motion within the work area WA or work space WS during the UV light being output during the pre-selected disinfection time period. After a lack of motion is again detected for a pre-selected time period (e.g. a pre-selected vacancy time period) in a third step S3, the output of visible light can be deactivated (e.g. turned off, stopped, etc.) in a fourth step S4. The UV light emission device 7b can be activated again to resume outputting of UV light to the work area or work space in the fourth step S4 as well. This can occur at the same time the visible light deactivation occurs or can occur at a different time after the visible light is turned off.

In some embodiments or modes of operation for the disinfection device, the UV light can be output in the work area WA or work space WS to resume the disinfection process as noted in step 5a in FIG. 13. For example, some embodiments, the UV light can be emitted continuously for the entirety of the pre-selected disinfection time period in a fifth step S5a. The dose of UV light that is applied can be relatively low so that the pre-selected disinfection time period is at least 60 minutes, at least 70 minutes, or at least 80 minutes in time and can range from 60 minutes to 120 minutes in duration, 60 minutes to 180 minutes in duration or from 60 minutes to 240 minutes duration. If no motion is detected in the work area WA or work space WS, then the UV light can be continuously emitted for the entirety of the pre-selected disinfection time period. Thereafter, the disinfection process can be completed. In some embodiments, an LED 9 or other indicator may be output via the disinfection device to indicate that the work area or work space was disinfected or to indicate that the disinfection cycle was successfully completed in a sixth step S6.

Alternatively, the UV light emission can be activated to output the UV light in the work area WA or work space WS to resume the disinfection process as noted in step 5b in FIG.

13. In such embodiments, the UV light can be emitted continuously for the remaining portion of the pre-selected disinfection time period in a fifth step S5b. For example, if the pre-selected disinfection time period is 150 minutes, and the UV light was output for 30 minutes before it was deactivated in step S2, then the UV light would be emitted for another 120 minutes so the cumulative time of UV light emission was the pre-selected disinfection time period of 150 minutes. This is an example of the resuming of disinfection via emission of the UV light where it left off can occur in response to no motion within the work area being detected for the pre-selected vacancy time period that can occur after interruption of the disinfection so the UV light is emitted to the work area or work space for the pre-selected disinfection time period. This option of step 5b contrasts with the option of step 5a, where the UV light is continuously emitted for the entirety of such a time period irrespective of how long the UV light may have been applied before the UV emission was stopped in step S2.

The dose of UV light that is applied can be relatively low so that the pre-selected disinfection time period is at least 60 minutes, at least 70 minutes, or at least 80 minutes in time and can range from 60 minutes to 120 minutes in duration, 60 minutes to 180 minutes in duration or from 60 minutes to 240 minutes duration. If no motion is detected in the work area WA or work space WS, then the UV light can be continuously emitted for the entirety of the pre-selected disinfection time period. Thereafter, the disinfection process can be completed. In some embodiments, an LED 9 or other indicator may be output via the disinfection device to indicate that the work area or work space was disinfected or to indicate that the disinfection cycle was successfully completed in a sixth step S6.

Embodiments of the process can utilize additional steps or modifications as well. For example, there can be an additional step between step S4 and steps S5a or step S5b for the exemplary process shown in FIG. 13 in which it is determined whether the UV light was emitted continuously for a pre-selected threshold level. If that threshold level was reached, then step S5b may be utilized. If that threshold level was not reached, then step 5a may be utilized.

Embodiments of the process shown in FIG. 13 can also include a maintenance step. For example, the UV tube for the UV light emission device 7b can be determined to need replacement based on seeing that indicia from the third LED 9c is being output by the disinfection device 1. This indicia may be seen through slot 31S for example. In response to seeing that indication, the baffle 31 can be worked on by personnel to replace the UV tube for the UV light emission device so a new UV tube replaces the old UV tube. After the new UV tube is used to replace the old UV tube, the disinfection device 1 can resume performance of the exemplary process shown in FIG. 13. The controller of the disinfection device 1 can also be configured to communicate an alert to indicate the UV tube needs replaced for providing a replacement notification to staff via an electronic message (e.g. email, text message, etc.). This type of messaging can help supplement the indicia provided by the third LED 9c, for example.

In some embodiments of the process, the process may only be initiated after a pre-selected disinfection time start threshold has been reached. This time can be a particular time that the controller can determine via a clock the controller may communicate with or run. The time can be a pre-selected time at which the work area or work space is not expected to be occupied (e.g. after 9 PM local time, after 10 PM local time, etc.). After disinfection has been performed, the controller can be configured to avoid use or actuation of further disinfection until the next time that the pre-selected disinfection time start time is reached.

It should be appreciated that the controller of the disinfection device 1 can be configured to run code or a program to perform an embodiment of the method for emission of UV light and/or light in a work space WS. The disinfection device 1 can perform the process when it runs the code stored in its memory via its processor CPU, for example. The emission of the UV light via the disinfection device 1 in the work space WS can provide the UV light within the distribution of light area DLA of the UV light emitted by the disinfection device 1. The pre-selected disinfection time period can be set so that location(s) or area farthest away from the UV light emitting mechanism 7b that is within the distribution of light area DLA for the UV light emitting mechanism 7b has a sufficient dose of UV light to kill one or more viruses or bacteria of interest or kill a pre-selected portion of such germs (e.g. 99% or 99.9% of such germs).

It should be appreciated that the first light emission device 7a and second light emission device 7b discussed herein uses the terms "first" and "second" as a naming convention to help identify these devices in the text. The first light emission device 7a can alternatively be considered a second light emission device and the second light emission device 7b can alternatively be considered a first light emission device.

Similarly, use of the terms "first", "second", and "third" used herein to refer to first LED 9a, second LED 9b, and third LED 9c is a naming convention to help identify different LEDs 9. The first LED 9a can alternatively be considered a second LED and the second LED 9b can alternatively be considered a first LED for example. As another example, the second LED 9b can alternatively be considered to be a third LED and the third LED 9c can be considered a second LED.

It should be appreciated that embodiments may be made or structured in a number of different ways to meet a particular set of design criteria. For example, the size and shape of the baffle 31, disinfection device 1, or lamp 7 can be adjusted to meet a particular set of design criteria. The type of indicia provided by LEDs 9 and mode indicator 11 can be adjusted as well to meet a particular set of design criteria (e.g. use of different colors, different sized LEDs, etc.). The size and shape of the mode indicator 11 can also be adjusted to meet a particular set of design criteria.

Thus, while certain exemplary embodiments of the furniture, lighting, ceiling mounted devices, baffles, disinfection devices positionable to disinfect work spaces within an office of an office building or other work area and methods of making and using the same have been shown and described above, it is to be distinctly understood that the invention is not limited thereto but may be otherwise variously embodied and practiced within the scope of the following claims.

What is claimed is:

1. A disinfection device positionable within a work area adjacent a ceiling above the work area, the disinfection device comprising:
   a housing;
   a controller positioned in the housing, the controller comprising a processor;
   a sensor communicatively connected to the controller, the sensor configured to detect motion within the work area;
   a lamp having an ultraviolet (UV) light emission device connected to the housing, the controller connected to the lamp to control an output of UV light from the UV light emission device to a work space within the work area, the output of the UV light emittable from the UV light emission device having a light distribution area within the work space;

the controller configured to detect a lack of motion for a pre-selected vacancy period of time within the work space and then activate the lamp so that the UV light emission device is activated to provide the UV light to the distribution of light area within the work space; and the controller also configured to deactivate emission of UV light after the sensor detects occupant motion while the UV light emission device is actively emitting UV light to stop output of the UV light and interrupt disinfection within a pre-selected disinfection time period based on the occupant motion.

2. The disinfection device of claim 1, wherein the UV light has a wavelength that is between 200 nm and 225 nm or is 222 nm.

3. The disinfection device of claim 1, comprising:
a plurality of light emitting diodes (LEDs) connectable to the housing, the LEDs include a first LED that is illuminable in a first color, a second LED illuminable in a second color, and a third LED illuminable in a third color.

4. The disinfection device of claim 1, wherein the sensor is connected to the housing and is positioned to detect motion within the work area that is below the disinfection device.

5. The disinfection device of claim 1, wherein, the controller is configured so that, after the interrupt of the disinfection, disinfection via emission of the UV light by the UV light emission device resumes where it left off to emit the UV light for the pre-selected disinfection time period after no motion within the work space is detected for the pre-selected vacancy time that occurs after the interrupt of the disinfection.

6. The disinfection device of claim 1, wherein, the controller is configured so that, after the interrupt of the disinfection within the pre-selected disinfection time period, the controller activates the UV light emission device to apply the UV light continuously for an entirety of the pre-selected disinfection time period after no occupant motion is detected for the pre-selected vacancy time after the interrupt of the disinfection.

7. The disinfection device of claim 1, wherein the UV light emission device is a first light emission device and the lamp also has a second light emission device, the second light emission device configured to output visible light to illuminate the work space.

8. The disinfection device of claim 1, wherein the UV light emission device is a first light emission device and the disinfection device also comprises a second light emission device connected to the housing that is configured to output visible light to illuminate the work space.

9. The disinfection device of claim 1, wherein the housing is rectangular in shape, polygonal in shape, or circular in shape and is configured to be mounted to a ceiling of a room of an office building.

10. A method of disinfecting a work area, comprising:
positioning at least one disinfection device adjacent a ceiling of the work area, each disinfection device comprising:

a housing;
a controller positioned in the housing, the controller comprising a processor;
a lamp having an ultraviolet (UV) light emission device connected to the housing, the controller connected to the lamp to control an output of UV light from the UV light emission device to a work space of the work area, the output of UV light emittable from the UV light emission device having a light distribution area within the work space;
detecting a lack of motion for a pre-selected vacancy period of time within the area and activating the lamp of the at least one disinfection device so that the UV light emission device provides the UV light to the distribution of light area within the work space;
detecting occupant motion while the UV light emission device is actively emitting UV light within a pre-selected disinfection time period and deactivating the UV light emission device to stop output of the UV light and interrupt disinfection based on the detected occupant motion.

11. The method of claim 10, comprising:
after the disinfection occurring within the pre-selected disinfection time period is interrupted, resuming disinfection via emission of the UV light where it left off for the pre-selected disinfection time period after no motion within the work space is detected for the pre-selected vacancy time period that occurs after interruption of the disinfection so the UV light is emitted to the work space for the pre-selected disinfection time period.

12. The method of claim 10, comprising:
after the disinfection occurring within the pre-selected disinfection time period is interrupted, activating the UV light emission device to apply the UV light continuously for an entirety of the pre-selected disinfection time period after no occupant motion is detected for the pre-selected vacancy time after the disinfection was interrupted so the UV light is emitted to the work space for the pre-selected disinfection time period.

13. The method of claim 10, wherein the disinfection device comprises a sensor to detect the occupant motion; and wherein the method comprises turning off an output of visible light in the work space after the lack of motion for the pre-selected vacancy period of time within the area is detected.

14. The method of claim 13, comprising:
emitting the visible light via the lamp of each of the at least one disinfection device to illuminate the space.

15. The method of claim 10, wherein the UV light has a wavelength of between 200 nm and 225 nm or has a wavelength of 222 nm.

16. The method of claim 10, wherein the work area is an office in an office building and there is at least one table positioned in the work space.

17. The method of claim 10, wherein the pre-selected disinfection time period is greater than 60 minutes and less than 240 minutes and the UV light emission device provides the UV light to the distribution of light area within the work space to provide a dose of at least 6 milliJoules per square centimeter (mJ/cm$^2$) to an entirety of the light distribution area within the pre-selected disinfection time period.

* * * * *